United States Patent [19]

Konig et al.

[11] 4,024,248

[45] May 17, 1977

[54] PEPTIDES HAVING LH-RH/FSH-RH ACTIVITY

[75] Inventors: Wolfgang Konig, Langenhain, Taunus; Rolf Geiger; Jurgen Kurt Sandow, both of Frankfurt am Main, all of Germany

[73] Assignee: Hoechst Aktiengesellschaft, Frankfurt am Main, Germany

[22] Filed: Aug. 7, 1975

[21] Appl. No.: 602,910

[30] Foreign Application Priority Data

Aug. 9, 1974 Germany .......................... 2438350

[52] U.S. Cl. ...................... 424/177; 260/112.5 LH
[51] Int. Cl.² ................ A61K 37/00; C07C 103/52
[58] Field of Search .......... 260/112.5 LH, 112.5 R; 424/177

[56] References Cited

UNITED STATES PATENTS

| | | |
|---|---|---|
| 3,896,104 | 7/1975 | McKinely et al. ............... 260/112.5 |
| 3,901,872 | 8/1975 | McKinely et al. ............... 260/112.5 |
| 3,914,412 | 10/1975 | Gendrich et al. .................. 424/177 |

OTHER PUBLICATIONS

Fujino et al, Biochem. Biophys. Res. Comm., 57, pp. 1248–1256, (1974).

*Primary Examiner*—Dolph H. Torrence
*Attorney, Agent, or Firm*—Curtis, Morris & Safford

[57] ABSTRACT

The present invention relates to peptides having strong LH-RH/FSH-RH activity, wherein Gly in the 6-position is replaced by different substituted amino acids and in the 10-position there is glycinamide or glycine in the 10-position is replaced by a NH-alkyl group with 1–3 carbon atoms or a NH-cyclopropyl group. The invention relates as well to a process for manufacturing said peptides, and to pharmaceutical preparations containing said peptides.

5 Claims, No Drawings

PEPTIDES HAVING LH-RH/FSH-RH ACTIVITY

The present invention relates to peptides having strong LH-RH/FSH-RH activity and to a process for their manufacture. The releasing hormone LH-RH/FSH-RH, which releases the luteotropic hormone (LH) and the follicle stimulating hormone (FSH), and which has the structure

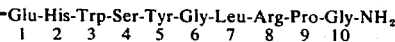
—Glu-His-Trp-Ser-Tyr-Gly-Leu-Arg-Pro-Gly-NH₂ (I)
  1    2    3   4   5   6   7   8   9   10

(Biochem. Biophys. Res. Commun. 43, 1334 (1971)) has been modified in many positions. Thereupon, it was found, that the activity was increased by replacing Gly in the 6-position by D-alanine (Biochemistry 12, 4616 (1973)) or by replacing Gly-NH₂ in the 10-position by ethyl amide, propyl amide or isopropyl amide (J. Med. Chem. 16, 1144 (1973)). When the two modifications are combined, analogues are obtained which have an even stronger activity (Biochem. Biophys. Res. Commun. 57, 335 (1974)). The successful exchange of Gly by D-amino acids was first demonstrated on insulin (Scientia Sinica XVI, 71–78 (1973)).

The replacement of glycine in the 6-position by D-amino acids having a stronger lipophilic activity, for example D-valine D-leucine or D-proline yielded analogues having a minor LH-RH activity (Abstracts of the Endocrine Society 55th Annual Meeting, 1973, page A 145). For this reason, it was very surprising that the exchange of glycine by strongly lipophilic unnatural D-amino acids that contain a tert.-butyl group yielded analogues having an even stronger activity than the analogues already known modified in the 6-position.

The invention relates to peptides of the general formula

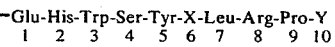
—Glu-His-Trp-Ser-Tyr-X-Leu-Arg-Pro-Y (I)
  1    2    3   4   5  6   7    8   9 10 in which X is D-Ser(Buᵗ), D-Thr(Buᵗ), D-Cys(Buᵗ), D-Asp(OBuᵗ), D-Glu(OBuᵗ), D-Orn(Boc or D-Lys(Boc) and Y is glycinamide an NH-alkyl group in which the alkyl radical contains from 1 – 3 carbon atoms, or the NH-cyclopropyl radical and which groups may be substituted by OH or fluorine atoms and, optinally, Ser⁴ may be replaced by Ala or Thr, Tyr by Phe, Leu⁷ by Ser(Buᵗ), Cys(BUᵗ), Asp(OBuᵗ), Orn(Boc) or Lys(Boc) and Arg by Orn, Lys or homoarginin.

A further object of the invention is a process for the manufacture of the peptides of the invention which comprises preparing these peptides a. by fragment condensation usual in peptide chemistry of peptide fragments according to the condensation scheme 1–3 + 4–10 or 1–2 + 3–10, or b. by stepwise synthesis, in which case other functional groups are blocked, optionally intermediately, by protective groups capable of being split off by hydrogenation or capable of being split off in an alkaline or slightly acid medium.

Analogues having an especially prolonged LH-RH activity are obtained if Leu is replaced, in addition to the modification of the invention, in the 6-position, by Ser(Buᵗ), Cys(Buᵗ), Asp(OBuᵗ) or Glu(OBuᵗ) and/or Y in the general formula I stands for an NH-alkyl group of 2 – 3 carbon atoms optionally substituted by fluorine.

Especially important are the compounds of the invention in which X stands for D-Ser(Buᵗ), D-Thr(Buᵗ), D-Cys(Buᵗ), D-Glu(OBuᵗ) or D-Asp(OBuᵗ). These compounds are orally active; peptides of this chain-length having oral activity have ot been known till now, which is especially surprising since the tert.-butyl ethers and tert.-butyl esters are unstable in an acid medium.

Compounds having a modification in the 6-position according to the invention are, for example, the following LH-RH analogues:

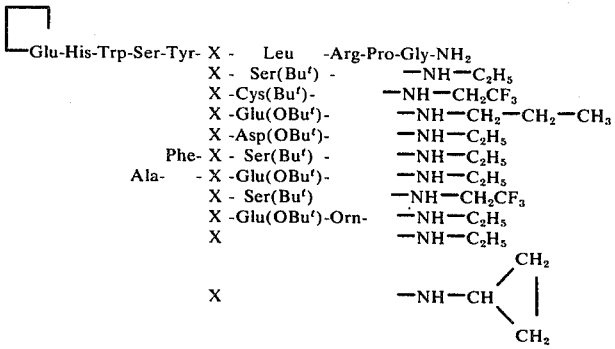

Of the compounds mentioned above are especially interesting those in which X stands for D-Ser(Buᵗ), D-Glu(OBuᵗ) and D-Asp(OBuᵗ).

In the synthesis of the compounds of the invention, only methods are applicable according to which, in the 6-position, the tert.-butyl radicals capable of easily being split off in an acid medium are not split off.

Fragment coupling according to (a) is preferably effected by means of azide coupling proceeding without racemization or by means of the DCC/1-hydroxybenzotriazole- or DCC/3-hydroxy-4-oxo-3,4-dihydro-1,2,3-benzotriazone method, or with the use of activated esters of fragments.

For the stepwise condensation of amino acids according to (b), activated esters of benzyloxycarbonylamino acids, for example N-hydroxysuccinimide esters or 2,4,5-trichlorophenyl are especially suitable and 4-nitrophenyl esters. The aminolysis of the two latter activated esters can very well be catalyzed by N-hydroxy compounds which have about the same acidity as acetic acid, for example 1-hydroxybenzotrizole.

Suitable intermediary protective groups are those which can be split off by hydrogenation, for example the benzyloxycarbonyl radical (= Z-radical) or which can be split off by means of weak acids, for example the 2-(p-diphenyl)-isopropyloxycarbonyl- or 2-(3,5-dimethoxyphenyl)-isopropyloxycarbonyl radical. In derivatives which contain Cys(Bu$^t$), the Z-radical is split off by hydrogenation with the addition of triethyl amine or N-ethyl morpholine.

The guanido function of the arginine can remain unprotected, or it can be blocked by a nitro group which split off in the following hydrogenation. But it can also be blocked by protective groups capable of being split off by means of acids, for example the carbobenzoxy radical or the tosyl radical, in which case, however, the protective groups have to be split off in the phase of the tetra peptide at the latest. For the nitro or tosyl group, liquid HF/anisol is suitable for this purpose. The same applies for an intermediary protection of the amide group by means of the 4,4'-dimethoxybenzhydryl radical, capable of being split off by means of acids, which is also split off at the latest in the phase of the tetrapeptide either by means of trifluoroacetic acid/anisol or together with a guanido protective group and/or an amino group capable of being split off by means of acids with HF/anisol.

As compared with 6-Gly analogues, but also with the 6-D-Ala analogues, the compounds of the invention showed a stronger and prolonged activity in the ovulation test and in the ascorbic acid depletion test. The surprising oral activity (dose: 0.01 − 0.2 mg/kg) of the compounds (X = D-Ser(Bu$^t$), D-Thr(Bu$^t$), D-Cys(Bu$^t$), D-Glu(OBu$^t$), D-Asp(OBu$^t$)) allow these medicaments to be used in a larger field of administration than the LH-RH, which is capable of being administered, so far, only via the parenteral or nasal route. They are novel medicaments which cause, in the case of insufficiency of the hypothalamus and hypophysis, the release of the luteinizing and the follicle stimulating hormone from the anterior lobe of the hypophysis and are, therefore, used for the treatment of female and male sterility in human beings and animals, as far as this sterility has a hypothalamic - hypophyseal origin. The compounds of this invention can also be applied for the determination of the ovulation time for women. Shortly before the expected ovulation time an ovulation can be caused for certain by the administration of the new medicaments. This is an important fact for family planning according to the Knaus-Ogino method as well as for artificial insemination.

Dissolved in a physiological sodium chloride solution, the compounds of the invention can be administered via the intravenous, the intramuscular or the subcutaneous route, the intranasal route in the form of nose drops or nose spray and also orally.

The doses preferably used in the various administration routes are:

| 20 | - | 1,000 ng/kg | intravenously |
| 20 | - | 2,000 ng/kg | subcutaneously |
| 20 | - | 10,000 ng/kg | intramuscularly |
| 100 | - | 50,000 ng/kg | intranasally |
| 10,000 | - | 200,000 ng/kg | perorally |

For process a) the following reaction schemes may be used:

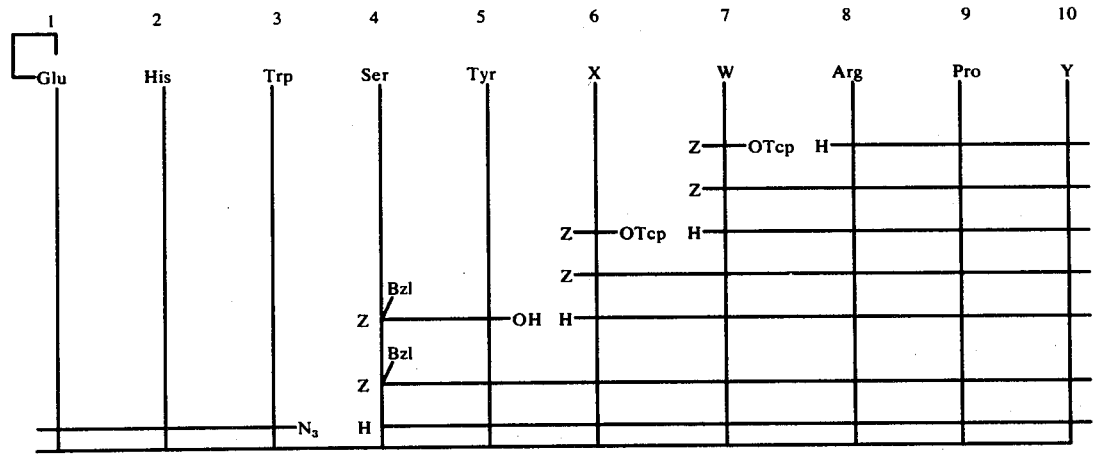

W = leucine and Y = NH—C$_2$H$_5$ (Examples 1 and 2)
W = Ser(Bu$^t$) and Y = NH—C$_2$H$_5$ (Example 3)
W = leucine and Y = NH—cyclopropyl (Example 5)

Reaction scheme 2

-continued

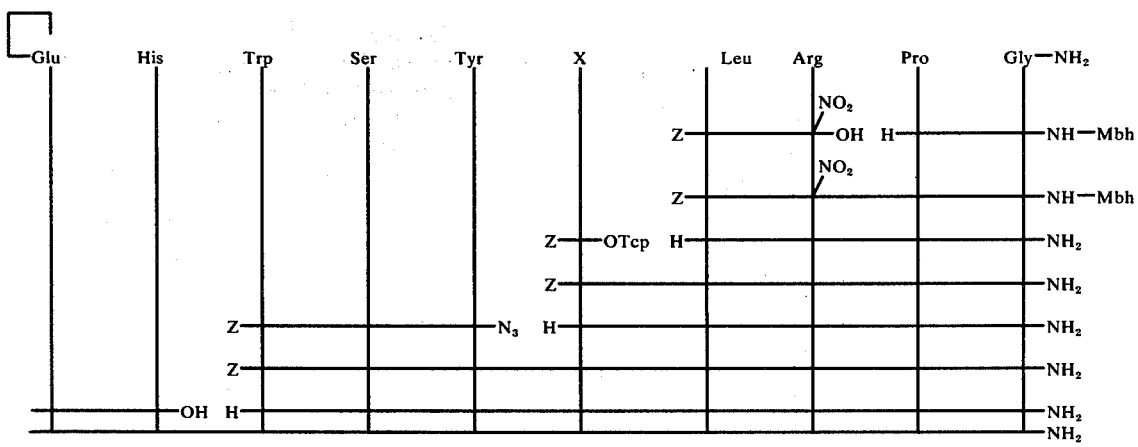

Abbreviations:

Bzl = benzyl
Boc = tert.-butyloxycarbonyl
Bu$^t$ = tert.-butyl
DCC = dicyclohexylcarbodiimide ⌐Glu = pyroglutamic acid
HOBt = 1-hydroxybenzotriazole
Mbh = 4,4-dimethoxybenzhydrol
OBu$^t$ = tert.-butyl ester
ONb = p-nitrobenzyl ester
ONSu = N-hydroxysuccinimide ester
OTcp = 2,4,5-trichlorophenyl ester
OOBt = 3-hydroxy-4-oxo-3,4-dihydro-1,2,3-benzotriazine ester
Z = benzyloxycarbonyl The following Examples illustrate the invention:

EXAMPLE 1

(In Analogy to Reaction Scheme 1):
⌐Glu-His-Trp-Ser-Tyr-D-Ser(Bu$^t$)-Leu-Arg-Pro-NH-C$_2$H$_5$ a. Z-Arg(Z$_2$)-Pro-NH-C$_2$H$_5$ To a solution of 8.9 g (50 mmoles) of H-Pro-NH-C$_2$H$_5$ · HCl, 28.9 g (50 mmoles) of Z-Arg(Z$_2$)-OH and 6.75 g (50 mmoles) of HOBt in 150 ml of methylene chloride were added, at 0° C, 6.5 ml of N-ethylmorpholine and 11 g of DCC. The mixture was stirred for 1 hour at 0° C and allowed to stand overnight at room temperature. The precipitate was suction-filtered and the filtrate was concentrated. The residue was dissolved in ethyl acetate and water. The ethyl acetate phase was shaken successively with saturated NaHCO$_3$-solution, 2 N H$_2$SO$_4$, saturated NaHCO$_3$-solution and with water, dried over Na$_2$SO$_4$ and concentrated. The residue was dissolved in isopropanol. Petroleum ether was used to precipitate an oil that crystallized overnight, Yield: 27.8 g (80%), melting point: 82°–85° C, $[\alpha]_D^{22} = -30.0°$ (c=1, methanol).

b. H-Arg-Pro-NH-C$_2$H$_5$ · 2 HCl 39.7 g (56.7 mmoles) of Z-Arg(Z$_2$)-Pro-NH-C$_2$H$_5$ were dissolved in 200 ml of methanol, a spatula tip of Pd/BaSO$_4$-catalyst was added and the solution was hydrogenated by allowing hydrogen to pass through the solution, while stirring. The pH of the solution was maintained at 4.5 by means of an autotitrator by adding 1 N methanolic hydrochloric acid. the catalyst was suction-filtered after hydrogenation was finished and the filtrate was concentrated. The residue was triturated with ether and suction-filtered. Yield: 17.9 g of amorphous substance (85%), $[\alpha]_D^{20} = -26.0°$ (c=1, methanol).

c. Z-Ser-Tyr(Bzl)-OH

To a suspension of 5.52 g (20 mmoles) of H-Tyr(Bzl)-OH in 60 ml of dimethyl acetamide were added 7.68 of z-Ser-OOBt and the suspension was stirred for 6 hours at room temperature. Undissolved substances were suction-filtered and to the filtrate, cooled to 0° C, were added 300 ml of water. The precipitate was suction-filtered, washed with dimethylacetamide/water mixture (1:10) and water and stirred with 1 N H$_2$SO$_4$. Suction-filtering, washing with water and drying followed. The precipitate was recrystallized from ethyl acetate/petroleum ether. Yield: 7.35 g (75%), melting point: 166° C, $[\alpha]_D^{20} = +20.9°$ (c=1, methanol).

d. Z-D-Ser(Bu$^t$)-Leu-Arg-Pro-NH-C$_2$H$_5$

To a solution of 11.2 g (30 mmoles) of H-Arg-Pro-NH-C$_2$H$_5$ · 2 HCl in 50 ml of dimethyl formamide were added, at 0° C, 7.8 ml of N-ethylmorpholine and 8.25 of Z-Leu-ONSu. The solution was allowed to stand overnight. It was concentrated and the residue was triturated once with ethyl acetate and once with ether. The solvents were decanted and the oil was dried under highly reduced pressure. The residue (20.0 g) was dissolved in methanol and hydrogenated catalytically in an analogous manner to Example 1 b). The residue was triturated with ether and dried under highly reduced pressure. 16.1 g of amorphous H-Leu-Arg-Pro-NHC$_2$H$_5$ · 2 HCl were obtained that contained salts as impurities (14.5 g = 100%, calculated on H-Arg-Pro-NH-C$_2$H$_5$ · 2 HCl).

2.45 g of that substance were dissolved, together with 675 mg of HOBt, 1.3 ml of N-ethyl morpholine and 2.4 g of Z-D-Ser(Bu$^t$)-OTcp in 20 ml of dimethyl formamide. The solution was allowed to stand overnight at room temperature and it was concentrated afterwards. The residue was triturated twice with saturated NaHCO$_3$-solution, dissolved in methylene chloride, dried over Na$_2$SO$_4$, concentrated and the residue was triturated with ether. Yield: 2.3 g (71%, calculated on H-Arg-Pro-NH-C$_2$H$_5$ · 2 HCl), melting point: 85–116° C.

e. H-Ser-Tyr-D-Ser(Bu$^t$)-Leu-Arg-Pro-NH-C$_2$H$_5$ · 2 HCl 2.3 g (3.33 mmoles) of Z-D-Ser(Bu$^t$)-Leu-Arg-Pro-NH-C$_2$H$_5$ were dissolved in methanol and hydrogenated catalytically in analogy to Example 1 b). The residue was triturated with ether and dried under highly reduced pressure. Yield: 1.93 g of amorphous material (93%).

The above 1.9 g (3.1 mmoles) of H-D-Ser(Bu$^t$)-Leu-Arg-Pro-NH-C$_2$H$_5$ · HCl were suspended together with 1.53 g (3.1 mmoles) of Z-Ser-Tyr(Bzl)-OH, 420 mg of HOBt and 0.8 ml of N-ethyl morpholine in 7 ml of dimethylformamide. At 0° C, 680 of DCC were added and the suspension was stirred for 1 hour at 0° C and was allowed to stand overnight at room temperature. The precipitate was suction-filtered the following day and the filtrate was concentrated. The residue was triturated twice with saturated NaHCO$_3$-solution, dissolved in methylene chloride and the solution was dried over Na$_2$SO$_4$ and concentrated. The residue was triturated with ether and suction-filtered. 2.65 g(= 2.57 mmoles) of Z-Ser Tyr(Bzl)-D-Ser(Bu$^t$)-Leu-Arg-Pro-NH-C$_2$H$_5$) of an amorphous substance were obtained, that were hydrogenated catalytically in analogy to Example 1 b). The residue was triturated with ether and dried under highly reduced pressure.

Yield: 2.2 g of amorphous H-Ser-Tyr-D-Ser(Bu$^t$)-Leu-Arg-Pro NH-C$_2$H$_5$ · 2 HCl (=2.5 mmoles) = 75%, calculated on Z-D-Ser(Bu$^t$) Leu-Arg-Pro-NH-C$_2$H$_5$.

For an analytical sample, 1.3 g of the product were purified by partition chromatography on the column as described hereinafter:

400 ml of glacial acetic acid, 800 ml of n-butanol and 4 liters of water were shaken. 300 ml of the upper phase were stirred with 240 g of Sephadex LH 20$^{(R)}$. The total of the solvent were absorbed. The contents of the column so pretreated was suspended in a corresponding amount of the lower phase. The suspension was allowed to swell for 3 hours and the column was filled (1 m × 4 cm). The lower phase was used for elution.

Yield of chromatographically pure substance: 562 mg $[-\alpha]_D^{22} = -43.9°$ (c=1, in methanol).

f. [Glu-His-Trp-Ser-Tyr-D-Ser(Bu$^t$)-Leu-Arg-Pro-NH-C$_2$H$_5$-diacetate

To a solution of 500 mg of [Glu-His-Trp-NH-NH$_2$ in 6 ml of dimethyl formamide were added, at −30° C, 0.66 ml of a 6.05 N HCl/dioxane solution and 1.2 ml of a 10% tert.-butyl nitrile solution in absolute dioxane. The solution was stirred for 20 minutes at −10° C and 877.8 mg of crude H-Ser-Tyr-D-Ser(Bu$^t$)-Leu-Arg-Pro-NH-C$_2$H$_5$ · 2 HCl and 0.78 ml of N-ethyl morpholine were added at −40° C. The mixture was allowed to stand overnight at 4° C. It was concentrated and the residue was triturated with ether. The substance was dissolved in water and chromatographed over Dowex$^{(R)}$ 1×2 (acetate form). The eluate was concentrated and purified over a carboxymethyl cellulose column (90 × 1.5 cm), that was equilibrated with 0.002 m NH$_4$-acetate solution. The substance was added as a solution in a 0.002 m NH$_4$-acetate solution. It was eluted with a 0.002 m NH$_4$-acetate solution in which the gradient of a 0.1 m NH$_4$-acetate solution was established (mixed volume 250 ml).

The fractions that contained the desired peptide were lyophilized twice. Yield: 401 mg of chromatographically pure substance. The content of peptide base was 76% as by UV-spectrum (yield: 25%). $[-\alpha]_C^{20} = -40.4°$ (c=1, in dimethyl acetamide).

g. [Glu-His-Trp-Ser-Tyr-D-Ser-Leu-Arg-Pro-NH-C$_2$H$_5$-diacetate (as comparison substance)

200 mg of [Glu-His-Trp-Ser-Tyr-D-Ser(Bu$^t$)-Leu-Arg-Pro-NH-C$_2$H$_5$-diacetate were dissolved with 0.1 ml of mercaptoethanol in 2 ml of trifluoroacetic acid. The solution was allowed to stand for 1 hour at room temperature, it was concentration and the residue was triturated with ether. The substance was suction-filtered and washed with ether, dissolved in water and chromatographed over Dowex 1×2 (acetate form). The eluate was concentrated and the residue was purified in analogy to Example 1 e) on Sephadex LH 20. Yield: 120 mg. The content of peptide base was 77.5% as per UV-spectrum $[-\alpha]_D^{20} = -43.7°$ (c=1, H$_2$O).

EXAMPLE 2

(analogous to reaction scheme 1):
[Glu-His-Trp-Ser-Tyr-D-Glu(OBu$^t$)-Leu-Arg-Pro-NH-C$_2$H$_5$ a. Z-D-Glu(OBu$^t$)-Leu-Arg-Pro-NH-C$_2$H$_5$ 2.45 g of H-Leu-Arg-Pro-NH-C$_2$H$_5$ · 2 HCl contaminated by salts were reacted in analogy to Example 1 d) with 2.6 g of Z-D-Glu(OBu$^t$)-OTcp, 675 g of HOBt and 1.3 ml of N-ethyl morpholine in 20 ml of dimethyl formamide. Yield: 2.75 g (81%, calculated on H-Arg-Pro-NH-C$_2$H$_5$ · 2 HCl), melting point: 83°–100° C.

b. H-Ser-Tyr-D-Glu(OBu$^t$)-Leu-Arg-Pro-NH-C$_2$H$_5$ · 2 HCl 1.85 g (2.53 mmoles) of Z-D-Glu(OBu$^t$)-Leu-Arg-Pro-NH-C$_2$H$_5$ were hydrogenated catalytically in methanol in analogy to Example 1 b). The residue was triturated with ether and suction-filtered. Yield: 1.7 g (99.5%).

The above 1.7 g (2.5 mmoles) of H-D-Glu(OBu$^t$)-Leu-Arg-Pro-NH-C$_2$H$_5$ · 2 HCl were reacted in analogy to Example 1 e) with 1.23 g of Z-Ser-Tyr(Bzl)-OH, 340 mg of HOBt, 0.65 ml of N-ethyl morpholine and 550 mg of DCC in 5 ml of dimethyl formamide. Yield: 2.8 g of slightly contaminated Z-Ser-Tyr(Bzl)-Glu(OBu$^t$)-Leu-Arg-Pro-NH-C$_2$H$_5$, which was hydrogenated catalytically in methanol in analogy to Example 1 b). The crude substance was purified by partition chromatography in analog to Example 2 e). Yield: 1.108 of chromatographically uniform product (47%, calculated on Z-D-Glu(OBu$^t$)-Leu-Arg-Pro-NH-C$_2$H$_5$). $[-\alpha]_D^{22} = -42.3°$ (c=1, in methanol).

c. [Glu-His-Trp-Ser-Tyr-D-Glu(OBu$^t$)-Leu-Arg-Pro-NH-C$_2$H$_5$-diacetate

In analogy to Example 1 f), 500 mg of Glu-His-Trp-NH-NH$_2$ were reacted with 920 mg (1 mmole) of H-Ser-Tyr-D-Glu(OBu$^t$)-Leu-Arg-Pro-NH-C$_2$H$_5$ · 2 HCl and purified chromatographically. Yield: 491.5 mg of chromatographically pure material. The content of peptide base was 79% as per UV-spectrum (yield: 30%). $[-\alpha]_D^{22} = -31.3°$ (c=1, dimethyl acetamide)

d. [Glu-His-Trp-Ser-Tyr-D-Glu-Leu-Arg-Pro-NH-C$_2$H$_5$-diacetate (as comparison substance)

190 mg of [Glu-His-Trp-Ser-Tyr-D-Glu(OBu$^t$)-Leu-Arg-Pro-NH-C$_2$H$_5$-diacetate were reacted and purified in analogy to Example 1 g). Yield: 148.9 mg. The content of peptide base was 85% as per UV-spectrum. $[\alpha]_D^{22} = -47.8°$ (c=1, in $H_2O$)

EXAMPLE 3

(in analogy to the reactor scheme 1):
⌈Glu-His-Trp-Ser-Tyr-D-Ser(Bu$^t$)-Ser(Bu$^t$)-Arg-Pro-NH-$C_2H_5$ a. H-Ser(Bu$^t$)-Arg-Pro-NH-$C_2H_5$ · 2 HCl To a solution of 2.23 g (mmoles) of H-Arg-Pro-NH-$C_2H_5$ · 2 HCl and 810 mg of HOBt in 10 ml of dimethyl formamide were added 1.56 ml of N-ethyl-morpholine and 3.12 g of Z-Ser(Bu$^t$)-OTcp and the solution was stirred for 2 hours at room temperature. Then, the solution was concentrated in vacuo. The residue was dissolved in ethyl acetate and the solution was shaken twice with saturated $NaHCO_3$ solution, dried over $Na_2SO_4$ and concentrated. The residue was triturated with ether and dried under highly reduced pressure. 2.3 g of amorphous substance were obtained that were hydrogenated catalytically in methanol in analogy to Example 1 b). Yield: 2.7 g (81%) of amorphous substance. According to thin-layer chromatography, the substance was not uniform (contamination by about 5 by-products).

b. H-D-Ser(Bu$^t$)-Ser(Bu$^t$)-Arg-Pro-NH-$C_2H_5$ · 2 HCl

To a solution of 2.57 g (5 mmoles) of H-Ser(Bu$^t$)-Arg-Pro-NH-$C_2H_5$ · 2 HCl and 675 mg of HOBt in 5 ml of dimethyl formamide were added, at 0° C, 1.3 ml of N-ethyl-morpholine and 2.37 g of Z-D-Ser(Bu$^t$)-OTcp. The solution was allowed to stand overnight. It was concentrated and the residue was dissolved in ethyl acetate. The solution was shaken twice with saturated $NaHCO_3$-solution, dried over $Na_2SO_4$ and concentrated. The residue was triturated with ether and dried under highly reduced pressure. Yield: 2.3 g of an amorphous substance which was hydrogenated catalytically in methanol in analogy to Example 1 b). The residue was triturated with ether. Yield: 2.05 g of an amorphous substance (62%, calculated on Z-D-Ser(Bu$^t$)-Otcp. The substance was further worked without further purification.

c. H-Ser-Tyr-D-Ser(Bu$^t$)-Ser(Bu$^t$)-Arg-Pro-NH-$C_2H_5$ · 2 HCl

To a solution of 2.0 g (3 mmoles) of H-D-Ser(Bu$^t$)-Ser(Bu$^t$)-Arg-Pro-NH-$C_2H_5$ · 2 HCl, 1.5 g of Z-Ser-Tyr(Bzl)-OH and 405 mg of HOBt in 5 ml of dimethylformamide were added, at 0° C, 0.78 ml of N-ethyl-morpholine and 660 mg of DCC. The solution was allowed to stand for 1 hour at 0° C and overnight at room temperature. The precipitate was suction-filtered and the filtrate was concentrated. The residue was dissolved in ethyl acetate and shaken three times with saturated $NaHCO_3$-solution. The ethyl acetate was concentrated without drying, because the peptide already precipitated. The resulting oil was hydrogenated catalytically in analogy to Example 1 b). Hydrogenation was carried out in a mixture of methanol and dimethyl-formamide. The crude product was purified chromatographically according to Example 1 e). Yield: 957 mg (35%, calculated on Z-Ser-Tyr(Bzl)-OH) of an amorphous substance. $[-\alpha]_D^{22} = -33.8°$ (c=1, in methanol).

d. ⌈Glu-His-Trp-Ser-Tyr-D-Ser(Bu$^t$)-Arg-Pro-NH-$C_2H_5$-diacetate

In analogy to Example 1 f), 250 mg of ⌈Glu-His-Trp-NH-$NH_2$ were reacted with 454 mg (0.5 mmole) of H-Ser-Tyr-Ser(Bu$^t$)-Ser (Bu$^t$)-Arg-Pro-NH-$C_2H_5$ and purified chromatographically. Yield: 321 mg. The content of peptide base was 75.5% as per UV-spectrum (38% yield). $[-\alpha]_D^{26} = -26.9°$ (c=1, in dimethyl formamide)

EXAMPLE 4

(In Analogy to the Reaction Scheme 2):
⌈Glu-His-Trp-Ser-Tyr-D-Lys(Boc)-Leu-Arg-Pro-Gly-$NH_2$ a. Z-Pro-Gly-NH-Mbh To a solution of 30.5 g (0.1 mole) of Z-Pro-Gly-$NH_2$ and 24 g (0.1 mole) of 4.4'-dimethoxybenzhydrole in 200 ml of glacial acetic acid were added 0.5 ml of concentrated $H_2SO_4$ and the solution was allowed to stand for one day at room temperature. Subsequently, an oil was precipitated with 850 ml of water which oil crystallized in the course of 24 hours. The substance was filtered off and dissolved in ethyl acetate. The ethyl acetate solution was shaken twice with saturated $NaHCO_3$-solution, dried with $Na_2SO_4$ and concentrated. The residue was crystallized from ethyl acetate/petroleum ether. Yield: 46.3 g (87%, melting point: 108° C, $[-\alpha]_D^{20} = -9.7°$ (c=1, in dimethyl formamide)

b. H-Pro-Gly-NH-Mbh · HCl 45 g (84.7 mmoles) of Z-Pro-Gly-NH-Mbh were hydrogenated catalytically in methanol in analogy to Example 1 b). The residue was triturated with ether. Yield: 33.7 g (91.5%), melting point: 233° C. A sample was reprecipitated from methanol/ether for analysis: melting point: 236° C, $[-\alpha]_D^{20} = -24.7°$ (c=1, in dimethyl acetamide)

c. Z-Leu-Arg($NO_2$)-OH

To a solution of 24.8 g (0.1 mole) of Z-Leu-OH, 26.9 g (0.1 mole) of H-Arg($NO_2$)-OMe · HCl and 13.5 g of HOBt in 200 ml of dimethyl formamide were added, at 0° C, 13 ml of N-ethyl morpholine and 22 g of DCC. The solution was stirred for 1 hour at 0° C and allowed to stand overnight at room temperature. The precipitate was suction-filtered, the filtrate was concentrated and the residue was taken up in ethyl acetate. The ethyl ester phase was shaken with saturated $NaHCO_3$-solution, 2 N $H_2SO_4$, saturated $NaHCO_3$-solution and water, dried over $Na_2SO_4$ and concentrated. The substance was triturated with diisopropyl ether. For further purification, the substance was dissolved in ethyl acetate and chromatographed over basic $Al_2O_3$. Yield: 23.05 g of amorphous substance.

19.2 g (40 mmoles) of the above substance were dissolved in 80 ml of dioxane. 16 ml of water were added and a spatula tip of thymolphthalein. 1 N of sodium hydroxide solution was slowly added dropwise, while stirring, until the solution turned definitely blue (consumption: 37.7 ml). Now, the solution was neutralized, concentrated and the residue was dissolved in ethyl acetate and 2 N HCl. The ethyl acetate phase was washed with water, dried with $Na_2SO_4$ and concentrated. It was triturated with diisopropyl ether and suction-filtered. Yield: 15.75 mg. Melting point: 147°-155° C, $[-\alpha]_D^{23} = -3.6°$ (c=1, in dimethyl acetamide)

d. Z-Leu-Arg($NO_2$)-Pro-Gly-NH-Mbh

To a solution of 4.66 g (10 mmoles) of Z-Leu-Arg($NO_2$)-OH, 4.34 g of H-Pro-Gly-NH-Mbh · HCl and 1.35 g of HOBt in 30 ml of dimethyl formamide were added, at 0° C, 1.3 ml of N-ethyl morpholine and 2.2 g of DCC. The solution was allowed to stand for 1 hour at 0° C and overnight at room temperature. The precipitate was suction-filtered and a substance was precipitated from the filtrate with water which substance was dissolved in ethyl acetate. The ethyl acetate solution was shaken with saturated NaHCO$_3$-solution, KHSO$_4$-solution and water. It was dried over Na$_2$SO$_4$ and concentrated. Yield: 6 g, melting point: 89°–93° C, $[-\alpha]_D^{23}$ = –21.7° (c=1, in dimethyl acetamide)

e. H-Leu-Arg-Pro-Gly-NH$_2$ · 2HF

To 6 g of Z-Leu-Arg(NO$_2$)-Pro-Gly-NH-Mbh and 12 ml of anisole 120 ml of HF were added. The mixture was stirred for 1 hour at 0° C, the HF was extracted in vacuo and the residue was dissolved in water and ether. The ether phase was shaken once with water. The combined water phases were washed with ether and lyophilized. Yield: 3.35 g of an amorphous substance. $[-\alpha]_D^{23}$ = –42.1° (c=1, in H$_2$O)

f. H-D-Lys(Boc)-Leu-Arg-Pro-Gly-NH$_2$ · 2 HCl

To a solution of 2.4 g (5 mmoles) of H-Leu-Arg-Pro-Gly-NH$_2$ · 2 HF and 675 mg of HOBt in 5 ml of dimethyl formamide were added at 0° C, 1.3 ml of N-ethyl morpholine and 2.8 g of Z-D-Lys(Boc)-OTcp. The solution was allowed to stand for 3 hours at room temperature, it was concentrated and the residue was triturated twice with saturated NaHCO$_3$-solution, dissolved in methylene chloride, dried over Na$_2$SO$_4$ and concentrated. The residue was triturated with ether and dried under highly reduced pressure. Yield: 3.1 g (77%) of amorphous substance. That substance was hydrogenated catalytically in methanol in analogy to Example 1 b). The residue was triturated with ether and dried under highly reduced pressure. Yield: 2.67 g (74%, calculated on Z-D-Lys(Boc)-OTcp) of amorphous substance that was not uniform according to thin-layer chromatography (contamination by two by-products).

g. H-Trp-Ser-Tyr-D-Lys(Boc)-Leu-Arg-Pro-Gly-NH$_2$ · 2 HCl

To a solution of 2.23 g (3.7 mmoles) of Z-Trp-Ser-Tyr-NH-NH$_2$ in 25 ml of dimethyl formamide were added, at –30° C, 2.44 ml of a 6.05 N HCl/dioxane solution and 4.45 ml of a 10% tert.-butylnitrite solution in absolute dioxane. The solution was stirred for 20 minutes at –10° and at –40° C 2.9 ml of N-ethylmorpholine and 26.7 g (3.7 mmoles) of H-D-Lys(Boc)-Leu-Arg-Pro-Gly-NH$_2$ were added. The mixture was allowed to stand overnight in a cooling chamber at 4° C. It was concentrated and the residue was triturated with ether. It was hydrogenated catalytically according to Example 1 b) and the crude substance was purified chromatographically on Sephadex LH 20 according to Example 1 e). Yield: 1.3 g (30%) of pure amorphous substance.

h. ⌈Glu-His-Trp-Ser-Tyr-D-Lys(Boc)-Leu-Arg-Pro-Gly-NH$_2$-diacetate

To a solution of 590 mg (0.5 mmole) of H-Trp-Ser-Tyr-D-Lys (Boc)-Leu-Arg-Pro-Gly-NH$_2$ · 2 HCl, 151 mg (0.5 mmole) of ⌈Glu-His-OH and 135 mg of HOBt in 5 ml of dimethyl formamide were added at 0° C, 0.13 ml of N-ethyl morpholine and 110 mg of DCC. The mixture was allowed to stand for 1 hour at 0° C and overnight at room temperature the precipitate was suction-filtered, concentrated and the residue was triturated with ether. It was dissolved in water, undissolved substances were filtered off and purification followed according to Example 1 f) over Dowex 1×2 and carboxymethyl cellulose, and then again on Sephadex LH 20 according to Example 1 e). Yield: 155 mg. The content of peptite was 78% as per UV-spectrum (17% yield). $[\alpha]_D^{23}$ = –39° (c=1, in dimethyl acetamide).

EXAMPLE 5

(In Analogy to Reaction Scheme 1)

⌈Glu-His-Trp-Ser-Tyr-D-Ser(Bu$^t$)-Leu-Arg-Pro-Cyclopropylamide a. Z-Pro-cyclopropylamide To a solution of 25 g (0.1 mole) of Z-proline, 13.5 g (0.1 mole) of HOBt and 5.71 g (0.1 mole) of cyclopropyl amine in 200 ml of absolute tetrahydrofurane were added, at 0° C, 22 g of DCC, dissolved in 50 ml of cold absolute tetrahydrofurane. The solution was stirred for 1 hour at 0° C and for 3 hours at room temperature, the precipitate was suction-filtered and the filtrate was concentrated. The oily residue was dissolved in ethyl acetate and shaken successively with saturated NaHCO$_3$-solution, 2 N HCl, NaHCO$_3$-solution and water, dried over Na$_2$SO$_4$ and concentrated. The residue was triturated with petroleum ether and suction-filtered. It was purified by recrystallization from ethyl acetate/petroleum ether. Yield: 23 g (= 80%). Melting point: 120°–123° C, $[\alpha]_D^{24}$ = 45.5° c=1, in methanol)

b. H-Pro-cyclopropyl amide . HCl

In analogy to Example 1 b), 19 g of Z-Pro-cyclopropyl amide were hydrogenated catalytically in methanol. The residue was triturated with ether. Yield: 11 g (88%), melting point: 169°–173° C.

c. Z-Arg(Z$_2$)-Pro-cyclopropylamide

To a solution of 28.85 g (50 mmoles) of Z-Arg(Z$_2$)-OH, 9.5 g (50 mmoles) of H-Pro-cyclopropyl amide . HCl and 6.75 g (50 mmoles) of HOBt in 100 ml of methylene chloride and 25 ml of dimethyl formamide were added 6.5 ml of N-ethyl morpholine and, at 0° C, a solution of 11 g of DCC in a small amount of methylene chloride. The solution was allowed to stand at 0° C for 1 hour and overnight at room temperature. The precipitate was suction-filtered and the filtrate was concentrated. The residue was taken up in ethyl acetate and washed with water, NaHCO$_3$-solution, 1 N HCl and NaHCO$_3$-solution, dried with Na$_2$SO$_4$ and concentrated, The residue was crystallized from ethyl acetate/petroleum ether. The crude substance (26.3 g) was purified chromatographically on a 250 g silica gel column in methylene chloride/acetone in the ratio 9:1 and 8:2. Yield: 22.2 g (62%), melting point: 171° C. $[\alpha]_D^{21}$ = –23.0° (c=1, in methanol)

d. H-Arg-Pro-cyclopropyl amide . 2 HCl 22 g (30.9 mmoles) of Z-Arg(Z$_2$)-Pro-cyclopropyl amide were hydrogenated catalytically in methanol according to Example 1 b). The residue was dried under highly reduced pressure. 11 g (89%) of an amorphous substance were obtained.

e. Z-D-Ser(Bu$^t$)-Leu-Arg-Pro-cyclopropyl amide

To a solution of 3.83 g (10 mmoles) of H-Arg-Pro-cyclopropylamide . 2 HCl in 20 ml of diemthylformamide were added, at 0° C, 2.6 ml of N-ethyl morpholine and 2.75 g of Z-Leu-ONSu. The solution was allowed to stand overnight at room temperature. It was concentrated and the residue was triturated once with ethyl acetate and once with ether. The solvents were decanted and the oil was dried under highly reduced pressure.

The residue was dissolved in methanol and hydrogenated catalytically as in Example 1 b). The residue was triturated with ether and dried under highly reduced pressure. 5.45 g of amorphous H-Leu-Arg-Pro-cyclopropylamide . 2 HCl were obtained that were contaminated by salts (4.96 g = 100%, calculated on H-Arg- Pro-cyclopropyl amide . 2 HCl). The total amount of substance was dissolved together with 1.35 g of HOBt, 2.6 ml of N-ethyl morpholine and 4.8 g of Z-D-Ser(-Bu$^t$)-OTcp in 20 ml of dimethylformamide. The solution was allowed to stand for 2 hours. It was concentrated and the residue was triturated twice with saturated NaHCO$_3$-solution, dissolved in methylene chloride, dried over Na$_2$SO$_4$, concentrated and the residue was triturated twice with saturated NaHCO$_3$-solution, dissolved in methylene chloride, dried over Na$_2$SO$_4$, concentrated and the residue was triturated with ether. Yield: 4.55 g (65%, calculated on H-Arg-Pro-cyclopropylamide . 2 HCl). The substance was amorphous and was further worked without any purification.

f. H-Ser-Tyr-D-Ser(Bu$^t$)-Leu-Arg-Pro-cyclopropyl amide . 2 HCl 3.5 g (5 mmoles) of Z-D-Ser(Bu$^t$)-Leu-Arg-Pro-cyclopropylamide were hydrogenated catalytically in methanol as in Example 1 b). The residue was triturated with ether and dried under highly reduced pressure. Yield: 3 g (94%) of amorphous substance.

The above 3 g of substance (4.7 mmoles) of H-D-Ser(Bu$^t$)-Leu-Arg-Pro-cyclopropyl amide . 2 HCl were dissolved together with 2.32 g (4.7 mmoles) of Z-Ser-Tyr(Bzl)-OH, 635 mg of HOBt and 1.22 ml of N-ethyl morpholine in 10 ml of dimethyl formamide. At 0° C, 1.04 g of DCC were added and the solution was allowed to stand for 1 hour at 0° C and overnight at room temperature. The precipitate was suction filtered the next day and the filtrate was concentrated. The residue was triturated twice with saturated NaHCO$_3$-solution, dissolved in methylene chloride solution and the solution was dried over Na$_2$SO$_4$ and concentrated. The residue was triturated with ether and suction-filtered. 3.5 g (71%) of Z-Ser-Tyr(Bzl)-D-Ser(Bu$^t$)-Leu-Arg-Pro-cyclopropyl amide were obtained that were hydrogenated catalytically according to Example 1 b). The residue was triturated with ether and dried under highly reduced pressure. Yield: 2.92 g (= 70%, calculated on Z-Ser-Tyr (Bzl)-OH). The crude substance was purified chromatographically on Sephadex LH 20 as has been described in Example 1 e). Yield: 1.4 g of chromatographically pure substance. $[\alpha]_D^{22} = -44.2°$ (c=1, in methanol).

g. ⌐Glu-His-Trp-Ser-Tyr-D-Ser(Bu$^t$)-Leu-Arg-Pro-cyclopropyl amidediacetate

In analogy to Example 1 f), 500 mg of ⌐Glu-His-Trp-NH-NH$_2$ were reacted with 890 mg of H-Ser-Tyr-D-Ser(Bu$^t$)-Leu-Arg-Pro-cyclopropyl amide . 2 HCl, worked up and purified. Yield: 420 mg of chromatographically pure substance. The content of peptide base was 77% as per UV-spectrum (yield: 32%). $[\alpha]_D^{20} = -40.8°$ (c=1, in dimethyl acetamide)

EXAMPLE 6

(Preparation for Oral Administration)

10 g of ⌐Glu-His-Trp-Ser-Tyr-D-Ser(Bu$^t$)-Leu-Arg-Pro-NH-C$_2$H$_5$-diacetate were triturated with 542 g of lactose. The trituration was mixed with 300 g of potato starch, moistened with an alcoholic solution of 8 g of gelatin and granulated. After drying, 60 g of potato starch, 10 g of magnesium stearate, 20 g of highly disperse silicon hydroxide and 60 g of talcum were admixed and the mixture was compressed to 10,000 tablets of each 150 mg weight. Each tablet contained 1 mg of active substance.

EXAMPLE 7

(Preparation for Intranasal Administration)

4.0 g of ⌐Glu-His-Trp-Ser-Tyr-D-Glu(OBu$^t$)-Leu-Arg-Pro-NH-C$_2$H$_5$-diacetate were dissolved in 100 ml of distilled water. At the same time, 31.2 g of NaHPO$_4$ . 2 H$_2$O, 66.29 g of Na$_2$HPO$_4$, 25 g of NaCl and 100 g of benzyl alcohol were dissolved in 8 l of distilled water and 500 g of polyvinyl alcohol having a K-value of about 90 were added. The two solutions were combined and filtered. The single dosage unit of 20μg was contained in 0.05 ml.

EXAMPLE 8

(Preparation for Intranasal Administration)

100 g of anhydrous lanolin and 440 g of vaseline were melted together. To the cold mass a suspension of 800 mg of microfine ⌐Glu-His-Trp-Ser-Phe-D-Ser(Bu$^t$)-Leu-Arg-Pro-NH-OCH$_3$-diacetate was added in 359.2 g of liquid paraffin. Finally, 10 g of benzyl alcohol were added and the ointment was homogenized. The single dosage unit of 40μg was contained in 0.05 g of ointment.

EXAMPLE 9

(Preparation for Injections)

2 mg of Glu-His-Trp-Ser-Tyr-D-Lys(Boc)-Leu-Arg-Pro-NH-C$_2$H$_5$-diacetate were dissolved in 500 ml of bidistilled water to which 100 ml of phosphate buffer of pH 4.5 were added. 1 g of mannitol and the calculated amount of NaCl were added to obtain isotonicity and the mixture was filled up with water to a volume of 1 liter. After filtration under sterile conditions, ampoules of 1 ml or 2 ml were filled up and lyophilized.

EXAMPLE 10

(Preparation for Injections)

The same procedure was effected as in Example 9. However before filling up with water, 2.5 g of 4-hydroxybenzoic acid methyl ester were added. After filtration under sterile conditions, ampoules of 1 ml or 2 ml were filled up.

What is claimed is:
1. A peptide of the formula

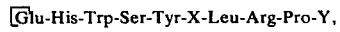

⌐Glu-His-Trp-Ser-Tyr-X-Leu-Arg-Pro-Y, wherein X is D-Ser (Bu$^t$), D-Cys (Bu$^t$), D-Asp (OBu$^t$), D-Glu (OBu$^t$), D-Orn (Boc), or D-Lys (Boc) and Y is glycinamide, NH-ethyl, or NH-cyclopropyl.

2. A compound as in claim 1 which is ⌐Glu-His-Trp-Ser-Tyr-D-Ser(Bu$^t$)-Leu-Arg-Pro-NH-C$_2$H$_5$.

3. A compound as in claim 1 which is ⌐Glu-His-Trp-Ser-Tyr-D-Glu(OBu$^t$)-Leu-Arg-Pro-NH-C$_2$H$_5$.

4. Pharmaceutical preparations for peroral, intranasal, intramuscular, subcutaneous, or intravenous administration to cause release of the luteinizing hormone (LH) and follicle stimulating hormone (FSH), said preparations comprising an effective amount of a compound as in Claim 1 in combination with a pharmaceutical carrier.

5. A pharmaceutical preparation as in claim 4 suitable for peroral administration.

* * * * *